US00PP21728P2

(12) United States Plant Patent
Gass

(10) Patent No.: US PP21,728 P2
(45) Date of Patent: Feb. 22, 2011

(54) ***HESPERALOE* PLANT NAMED 'PERFU'**

(50) Latin Name: ***Hesperaloe funifera*×*Hesperaloe parviflora***
Varietal Denomination: Perfu

(76) Inventor: Ronald E. Gass, P.O. Box 2500, Litchfield Park, AZ (US) 85340

( * ) Notice: Subject to any disclaimer, the term of this patent is extended or adjusted under 35 U.S.C. 154(b) by 0 days.

(21) Appl. No.: 12/584,120

(22) Filed: Aug. 31, 2009

(51) Int. Cl.
*A01H 5/00* (2006.01)

(52) U.S. Cl. ..... Plt./263.1
(58) Field of Classification Search ..... Plt./263.1, Plt./226

See application file for complete search history.

*Primary Examiner*—June Hwu
(74) *Attorney, Agent, or Firm*—C. A. Whealy

(57) ABSTRACT

A new and distinct cultivar of *Hesperaloe* plant named 'Perfu', characterized by its upright plant habit; vigorous growth habit; tall and erect pink-colored peduncles; campanulate pink-colored flowers with flared apices; and good garden performance.

1 Drawing Sheet

Botanical designation: *Hesperaloe funifera*×*Hesperaloe parviflora.*

Cultivar denomination: 'PERFU'.

BACKGROUND OF THE INVENTION

The present invention relates to a new and distinct cultivar of *Hesperaloe* plant, botanically known as *Hesperaloe funifera*×*Hesperaloe parviflora* and hereinafter referred to by the name 'Perfu'.

The new *Hesperaloe* plant is a product of a planned breeding program conducted by the Inventor in Tucson, Ariz. The objective of the breeding program is to develop new *Hesperaloe* plants with unique flower form and color.

The new *Hesperaloe* plant originated from a cross-pollination in 1997 of an unnamed selection of *Hesperaloe funifera,* not patented, as the female, or seed, parent with an unnamed selection of *Hesperaloe parviflora,* not patented, as the male, or pollen, parent. The new *Hesperaloe* plant was discovered and selected by the Inventor in 2002 as a single flowering plant within the progeny of the stated cross-pollination in a controlled environment in Phoenix, Ariz.

Asexual reproduction of the new *Hesperaloe* plant by tissue culture in a controlled greenhouse environment Phoenix, Ariz. has shown that the unique features of this new *Hesperaloe* plant are stable and reproduced true to type in successive generations of asexual reproduction.

SUMMARY OF THE INVENTION

Plants of the new *Hesperaloe* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Perfu'. These characteristics in combination distinguish 'Perfu' as a new and distinct cultivar of *Hesperaloe:*

1. Upright plant habit.
2. Vigorous growth habit.
3. Tall and erect pink-colored peduncles.

4. Campanulate pink-colored flowers with flared apices.
5. Good garden performance.

Plants of the new *Hesperaloe* can be compared to plants of the female parent selection. Plants of the new *Hesperaloe* differ from plants of the female parent selection in the following characteristics:

1. Plants of the new *Hesperaloe* have shorter leaves than plants of the female parent selection.
2. Flowers of plants of the new *Hesperaloe* are pink in color whereas flowers of plants of the female parent selection are creamy white in color.
3. Peduncles of plants of the new *Hesperaloe* are shorter than plants of the female parent selection.
4. Peduncles of plants of the new *Hesperaloe* are vertically orientated whereas peduncles of plants of the female parent selection are outwardly orientated.
5. Peduncles of plants of the new *Hesperaloe* are pink in color whereas peduncles of plants of the female parent selection are green in color.

Plants of the new *Hesperaloe* can be compared to plants of the male parent selection. Plants of the new *Hesperaloe* differ from plants of the male parent selection in the following characteristics:

1. Flowers of plants of the new *Hesperaloe* are pink in color whereas flowers of plants of the male parent selection are coral red in color.
2. Peduncles of plants of the new *Hesperaloe* are vertically orientated whereas peduncles of plants of the male parent selection are outwardly orientated.
3. Peduncles of plants of the new *Hesperaloe* are pink in color whereas peduncles of plants of the male parent selection are green in color.

Plants of the new *Hesperaloe* can be compared to plants of the *Hesperaloe parviflora* 'Perpa', disclosed in U.S. Plant patent application Ser. No. 12/583,681. Plants of the new *Hesperaloe* differ from plants of 'Perpa' in the following characteristics:

1. Plants of the new *Hesperaloe* are larger than plants of 'Perpa'.
2. Plants of the new *Hesperaloe* have larger leaves than plants of 'Perpa'.

3. Plants of the new *Hesperaloe* and 'Perpa' differ in leaf color.
4. Flowers of plants of the new *Hesperaloe* are pink in color whereas flowers of plants of 'Perpa' are red in color.

BRIEF DESCRIPTION OF THE PHOTOGRAPHS

The accompanying colored photographs illustrate the overall appearance of the new *Hesperaloe* plant, showing the colors as true as it is reasonably possible to obtain in colored reproductions of this type. Colors in the photographs may differ slightly from the color values cited in the detailed botanical description which accurately describe the colors of the new *Hesperaloe* plant.

The photograph at the top of the sheet is a close-up view of a typical inflorescence of 'Perfu'.

The photograph at the bottom of the sheet is a side perspective view of a typical plant of 'Perfu' grown in a container.

DETAILED BOTANICAL DESCRIPTION

The aforementioned photographs and following observations, measurements and values describe plants of the new *Hesperaloe* grown in 30.5-cm containers in Cochise County, Ariz. during the summer in an outdoor nursery and under conditions which closely approximate commercial production. During the production of the plants, day temperatures ranged from 32° C. to 40° C. and night temperatures ranged from 18° C. to 27° C. Plants were five years old when the photographs and the description were taken. In the description, color references are made to The Royal Horticultural Society Colour Chart, 2007 Edition, except where general terms of ordinary dictionary significance are used.

Botanical classification: *Hesperaloe funifera*×*Hesperaloe parviflora* 'Perfu'.

Parentage:

*Female, or seed, parent.*—Unnamed selection of *Hesperaloe funifera,* not patented.

*Male, or pollen, parent.*—Unnamed selection of *Hesperaloe parviflora,* not patented.

Propagation:

*Type.*—By tissue culture.

*Root description.*—Fibrous; tough.

Plant description:

*Plant form and growth habit.*—*Herbaceous* plant; upright plant habit; vigorous growth habit; leaves arranged in a basal rosette with a tall erect central flower stalk.

*Plant height, from soil level to top of inflorescence.*—About 224 cm.

*Plant height, from soil level to top of foliar plane.*—About 64 cm.

*Plant diameter* (*area of spread*).—About 76 cm.

Stem description:

*Internode length.*—About 6 mm.

*Texture.*—Smooth, glabrous.

*Color.*—Close to 157D.

Foliage description:

*Arrangement.*—In a basal rosette, whorled; simple; sessile.

*Length.*—About 82 cm.

*Width.*—At the apex, close to 2.5 mm; mid-section, about 1.8 cm; at the base, about 5.6 cm.

*Shape.*—Elongated lanceolate.

*Apex.*—Acuminate.

*Base.*—Clasping the stem.

*Margin.*—Entire; filiferous.

*Texture, upper and lower surfaces.*—Smooth, glabrous; rigid, tough; longitudinally ridged.

*Venation pattern.*—Parallel.

*Color.*—Developing leaves, upper surface: Close to 146D. Developing leaves, lower surface: Close to 146C. Fully expanded leaves, upper surface: Close to 146D; towards the apex, overlain with close to 173B to 173C; towards the base, close to 13B; venation, close to 146D. Fully expanded leaves, lower surface: Close to 146C; towards the apex, overlain with close to 173B to 173C; towards the base, close to 13B; venation, close to 146C.

Flower description:

*Flower appearance/arrangement.*—Single campanulate flowers arranged in terminal upright racemes; flowers with flared petal apexes; freely flowering habit with usually about 1,000 flowers per inflorescence; flowers initially face upright and then face outwardly with development.

*Natural flowering season.*—Continuous flowering from March to mid to late summer in Arizona.

*Flower longevity.*—Individual flowers last about seven to ten days on the plant; flowers not persistent.

*Fragrance.*—None detected.

*Inflorescence height.*—About 58 cm.

*Inflorescence diameter.*—About 5.5 cm.

*Flower length.*—About 1.7 cm.

*Flower diameter.*—About 2 cm.

*Flower bud.*—Length: About 1.8 cm. Diameter: About 6 mm. Shape: Oblong. Color: Close to 55B.

*Flower segments.*—Quantity per flower: Six segments fused towards the base; apices flared. Length: About 1.9 cm. Width: About 5 mm. Shape: Elliptical, narrow. Apex: Acute; reflexed. Margin: Entire. Texture, upper and lower surfaces: Smooth, glabrous. Color: When opening, upper surface: Close to 49D. When opening, lower surface: Close to 55B. Fully opened, upper surface: Close to 75C to 75D; color becoming closer to 62D with development. Fully opened, lower surface: Close to 67C to 67D; color becoming closer to 70D with development.

*Peduncles.*—Length: About 124 cm. Diameter: About 1.3 cm. Strength: Strong. Aspect: Erect. Texture: Smooth, glabrous. Color: Lighter than 182D.

*Pedicels.*—Length: About 9 mm. Diameter: About 1 mm. Strength: Strong. Aspect: About 30° to 45° from peduncle axis. Texture: Smooth, glabrous. Color: Close to 183D.

*Reproductive organs.*—Androecium: Quantity per flower: About six. Filament length: About 1.1 cm. Filament color: Close to 75D. Anther shape: Oblong to lanceolate. Anther length: About 5 mm. Anther color: Close to 6D. Amount of pollen: Moderate. Pollen color: Close to 13A. Gynoecium: Quantity per flower: One. Pistil length: About 1.4 cm. Style length: About 7 mm. Style color: Close to NN155D. Stigma appearance: Capitate. Stigma color: Close to NN155D. Ovary color: Close to 1D.

*Seeds.*—Quantity per flower: About 60. Length: About 9 mm. Diameter: About 7 mm. Color: Close to 159D.

*Fruits.*—Type: Tri-locular capsule. Length: About 2.7 cm. Diameter: About 2.3 cm. Texture: Smooth, glabrous. Color: Close to 146C.

Garden performance: Plants of the new *Hesperaloe* have been observed to have good garden performance and to tolerate rain, wind and temperatures ranging from about −20° C. to about 50° C.

Pathogen/pest resistance: Plants of the new *Hesperaloe* have not been observed to be resistant to pathogens and pests common to *Hesperaloe*.

It is claimed:

1. A new and distinct *Hesperaloe* plant named 'Perfu' as illustrated and described.

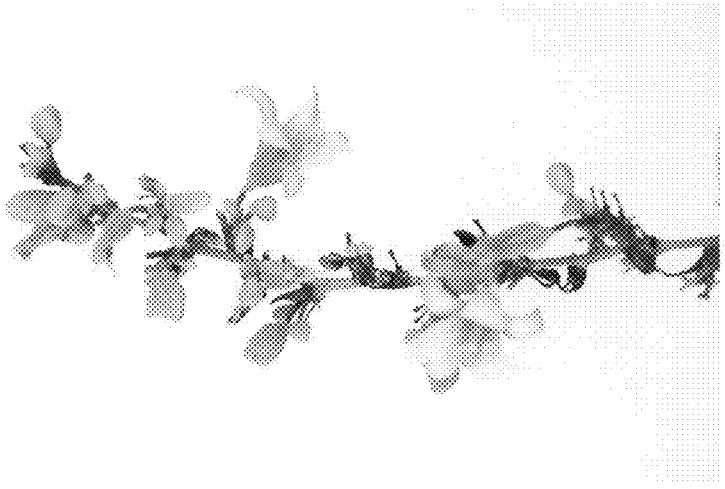
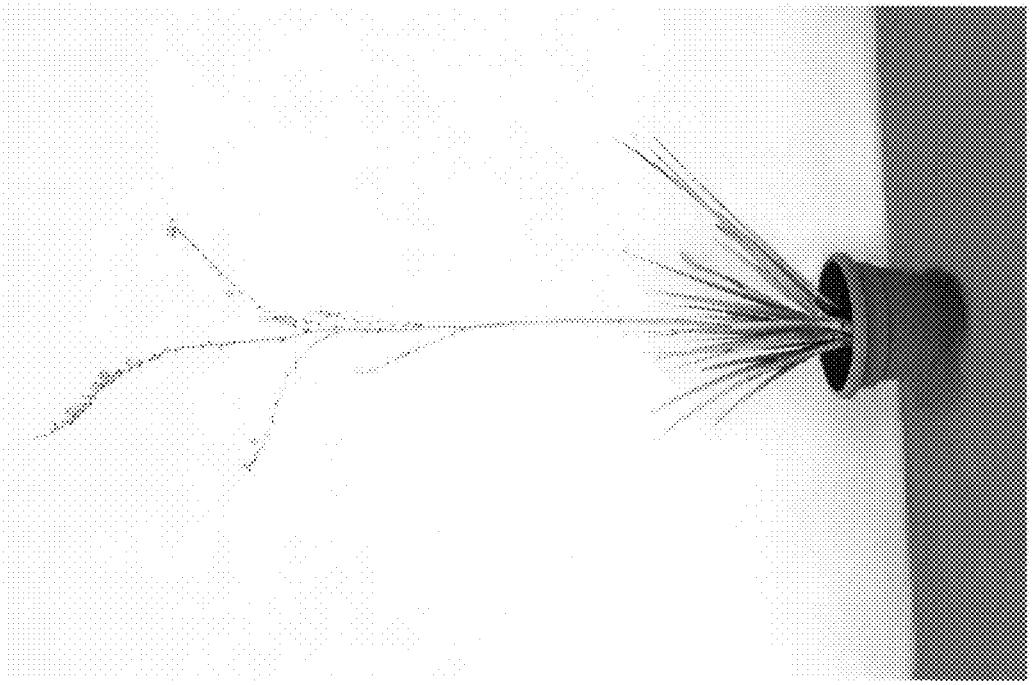

* * * * *